United States Patent
Old et al.

(10) Patent No.: US 7,576,112 B2
(45) Date of Patent: *Aug. 18, 2009

(54) THERAPEUTIC N-ARYL OR N-HETEROARYL PYRAZOLIDINE AND PYRAZOLIDINONE DERIVATIVES

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/372,321

(22) Filed: Feb. 17, 2009

(65) Prior Publication Data

US 2009/0163560 A1 Jun. 25, 2009

Related U.S. Application Data

(63) Continuation of application No. 11/836,094, filed on Aug. 8, 2007, now Pat. No. 7,507,833.

(60) Provisional application No. 60/821,994, filed on Aug. 10, 2006.

(51) Int. Cl.
- *A61K 31/41* (2006.01)
- *A61K 31/415* (2006.01)
- *C07D 257/00* (2006.01)
- *C07D 231/00* (2006.01)

(52) U.S. Cl. ........... 514/381; 514/382; 514/406; 548/251; 548/252; 548/253; 548/364.1

(58) Field of Classification Search ............ 548/251, 548/252, 253, 364.1; 514/381, 382, 406
See application file for complete search history.

(56) References Cited

U.S. PATENT DOCUMENTS 5,902,726 A 5/1999 Kliewer et al.

FOREIGN PATENT DOCUMENTS

| EP | 1481976 | 3/2003 |
|---|---|---|
| WO | WO 2004/043354 | 5/2004 |

OTHER PUBLICATIONS

Baxter, et al., "Synthesis and Use of 7-Substituted Norbornadienes + for the Preparation of Prostaglandins and Prostanoids," J. Chem. Soc. Perkin Trans., 1986, pp. 889-900.
Dragoli, et al., "Parallel Synthesis of Prostaglandin $E_1$ Analogues," J. Comb. Chem., 1999, 1, pp. 534-539.
Stella, Valentino J, Expert Opinion of Therapeutic Patents, Prodrugs as therapeutics, 2004 14(3): 277-280.
Wolff et al. (Burger's Medicinal Chemistry, 5th Ed., vol. 1, pp. 975-977, 1994)l.
Testa, Bernard, Biochemical Pharmacology, Prodrug Research: futile or fertile? 68 (2004) 2097-2106.
Ettmayer, Peter, Medicinal Chemistry, Lessons Learned from Marketed and Investigational Prodrugs, 47(10)(2004)2394-2404.

*Primary Examiner*—Kamal A Saeed
*Assistant Examiner*—Samantha L Shterengarts
(74) *Attorney, Agent, or Firm*—Allergan, Inc.; Kevin Forrestal

(57) ABSTRACT

A compound having a structure

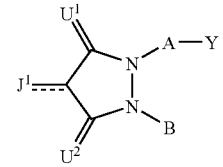

and therapeutic methods, compositions, and medicaments related thereto are disclosed herein.

17 Claims, No Drawings

THERAPEUTIC N-ARYL OR N-HETEROARYL PYRAZOLIDINE AND PYRAZOLIDINONE DERIVATIVES

RELATED APPLICATION

This application is a continuation of U.S. patent application Ser. No. 11/836,094, filed Aug. 8, 2007, now U.S. Pat. No. 7,507,833 which claims the benefit of U.S. provisional patent application Ser. No. 60/821,994, filed on Aug. 10, 2006, each of which is incorporated herein by reference in its entirety.

DESCRIPTION OF THE INVENTION

Disclosed herein is a compound having a structure

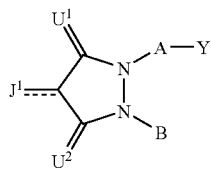

or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH=CH—(CH_2)_3$—, or —$CH_2C≡C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

$U^1$ and $U^2$ are independently hydrogen, O, or S.

$J^1$ is H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$; and B is substituted aryl or substituted heteroaryl.

Also disclosed herein is a carboxylic acid or a bioisostere thereof, said carboxylic acid having a structure

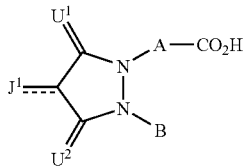

or a pharmaceutically acceptable salt thereof, or a prodrug thereof;

wherein a dashed line represents the presence or absence of a bond;

A is —$(CH_2)_6$—, cis —$CH_2CH=CH—(CH_2)_3$—, or —$CH_2C≡C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;

$U^1$ and $U^2$ are independently hydrogen, O, or S;

$J^1$ is H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$; and B is substituted aryl or substituted heteroaryl.

"Bioisosteres are substituents or groups that have chemical or physical similarities, and which produce broadly similar biological properties." Silverman, Richard B., *The Organic Chemistry of Drug Design and Drug Action*, $2^{nd}$ Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids mentioned above comprising up to 14 carbon atoms is also contemplated. In an ester, a hydrocarbyl moiety replaces a hydrogen atom of an acid such as in a carboxylic acid ester, e.g. $CO_2Me$, $CO_2Et$, etc. In another embodiment, in an ester, a hydroxyethyl moiety replaces a hydrogen atom of an acid, e.g., $CO_2CH_2CH_2OH$.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

Carboxylic Acid Bioisosteres According to Han et. al.

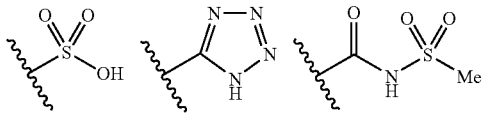

-continued

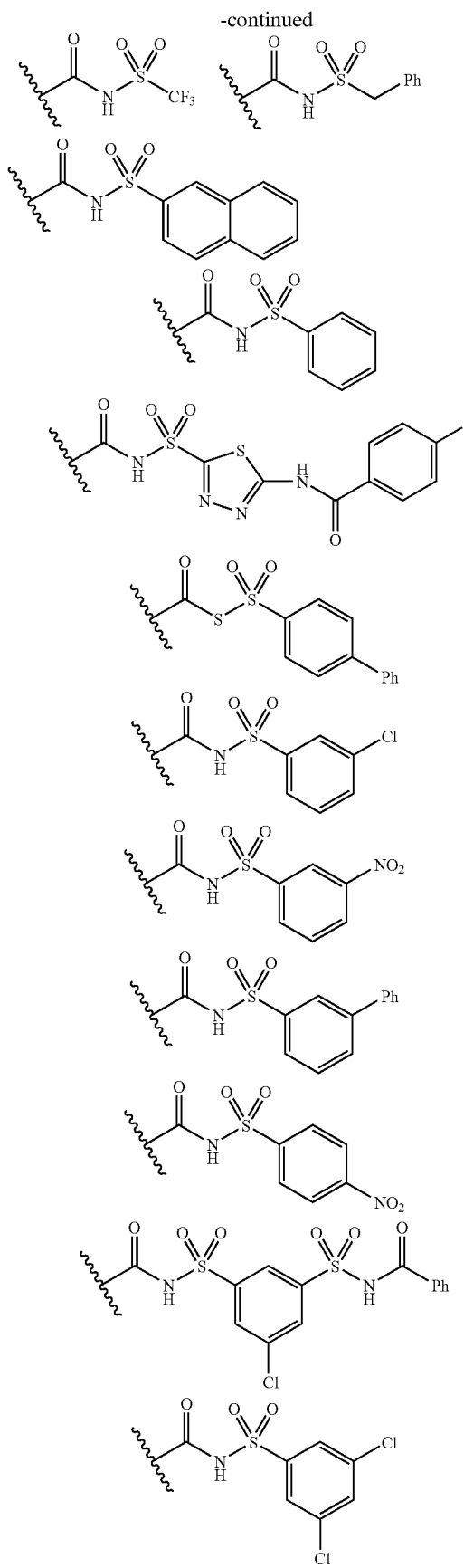

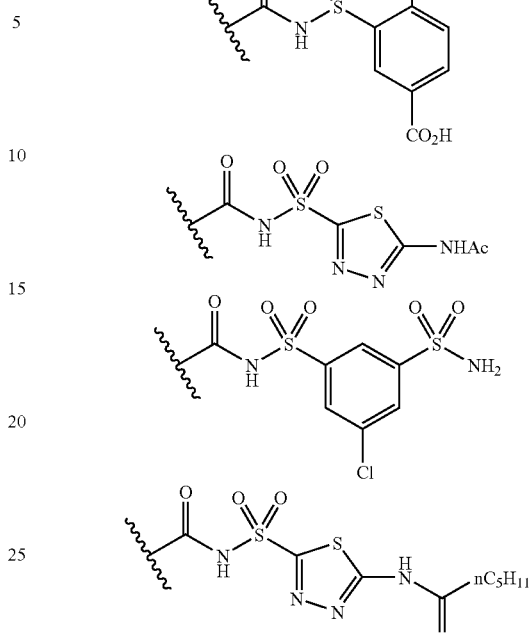

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

| Y is tetrazolyl. | | |
|---|---|---|
| Organic Acids | Esters | Amides |
| $M^1$—$CO_2H$ Carboxylic Acid | $M^1$—$CO_2R$ Carboxylic Acid Ester | $M^1$—$CO_2NR_2$ Carboxylic Acid Amide |
| $M^1$—$P(O)(OH)_2$ | $M^1$—$P(O)(OH)R$ | $M^1$—$P(O)(OH)NR_2$ |

-continued

Y is tetrazolyl.

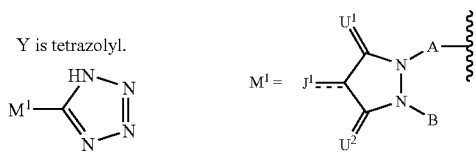

| Organic Acids | Esters | Amides |
|---|---|---|
| Phosponic Acid | Phosphonic Acid Ester | Phosphonic Acid Amide |
| $M^1$—$SO_3H$ | $M^1$—$SO_3R$ | $M^1$—$SO_3NR_2$ |
| Sulfonic Acid | Sulfonic Acid Ester | Sulfonic Acid Amide |
| $M^1$—$CH_2OH$ | $M^1$—$CH_2OR$ | |
| Y is hydroxymethyl | Ether | |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

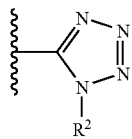

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

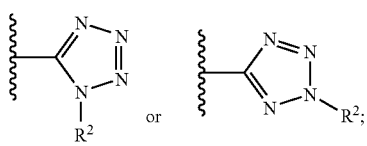

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

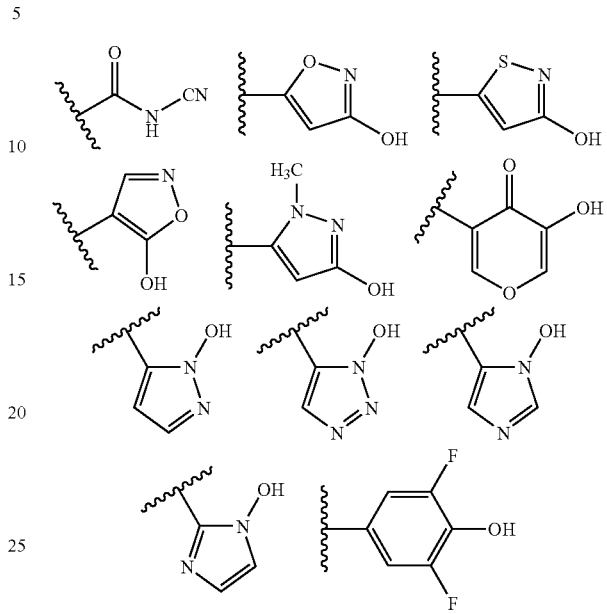

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (*Eur. J. Med. Chem.* 1996, 31, 417-425) as carboxamide replacements having improved in vivo efficacy at the benzodiazepine receptor.

Carboxylic Acid Bioisosteres According to Orlek et. al.

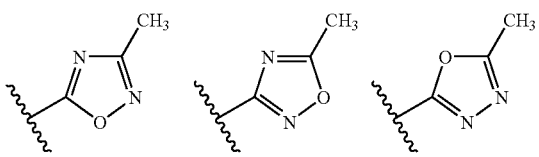

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.

Tetrazole Bioisosteres According to Kohara et. al.

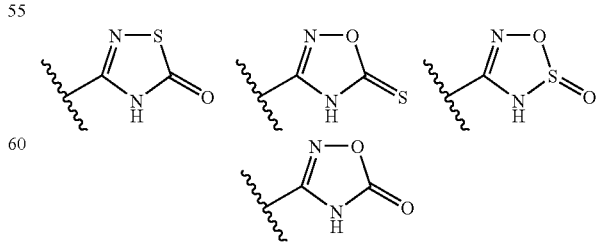

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.

Carboxylic Acid Bioisosteres According to Drysdale et. al.

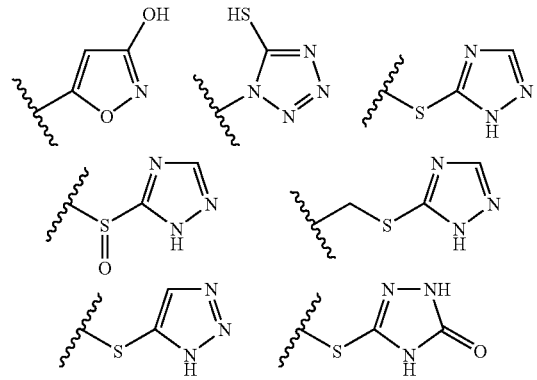

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH=CH— or —C≡C—.

Thus, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in that any carbon is replaced with S or O. For example, A may be a moiety where S replaces one or two carbon atoms such as one of the following or the like.

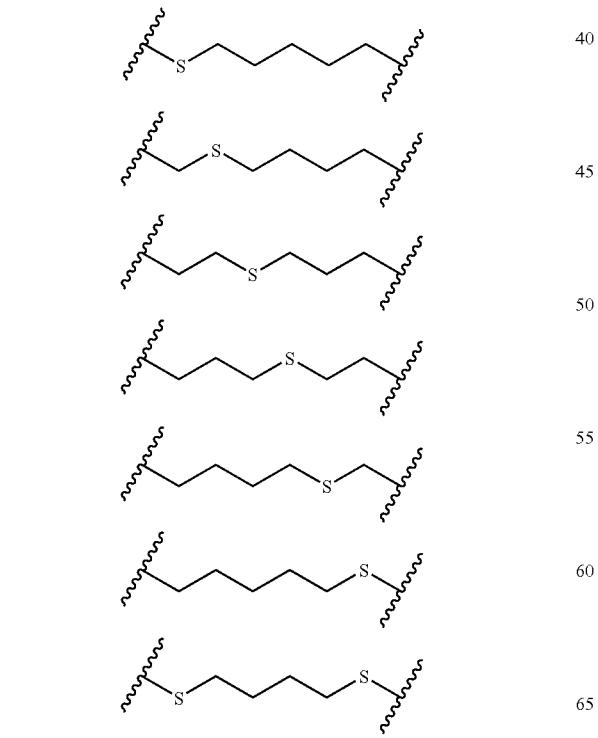

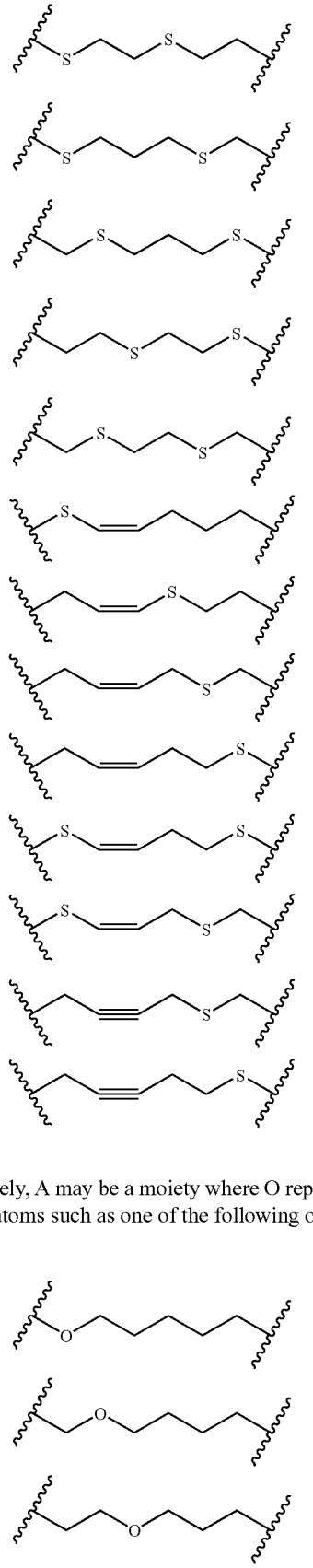

Alternatively, A may be a moiety where O replaces one or two carbon atoms such as one of the following or the like.

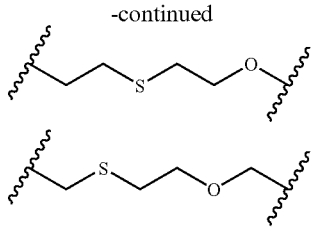

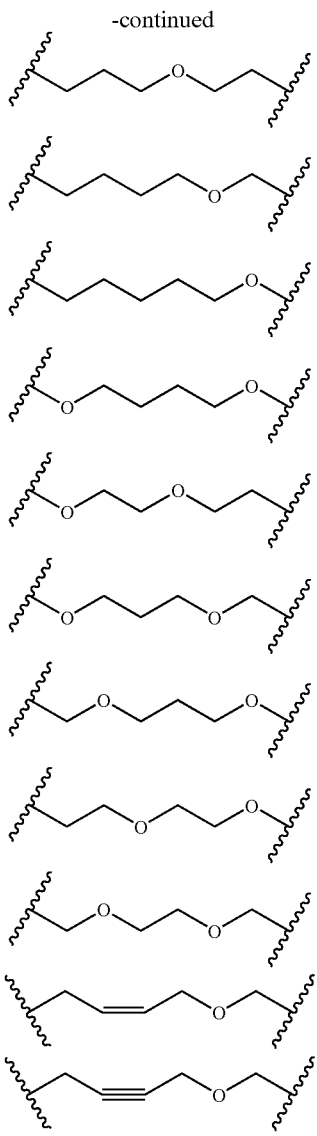

Alternatively, A may have an O replacing one carbon atom and an S replacing another carbon atom, such as one of the following or the like.

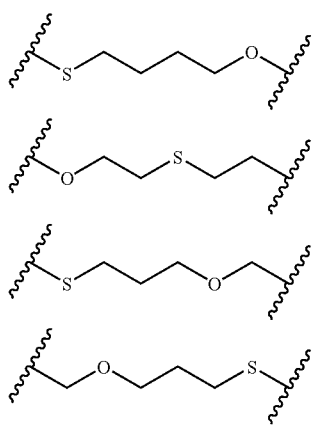

Alternatively, in certain embodiments A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$— may be replaced by —CH═CH— or —C≡C—. In other words, in one embodiment A comprises:

1) a) 1, 2, 3, or 4 —CH$_2$— moieties, or
   b) 0, 1 or 2 —CH$_2$— moieties and —CH═CH— or —C≡C—; and
2) Ar;
e.g. —CH$_2$—Ar—, —(CH$_2$)$_2$—Ar—, —CH═CH—Ar—, —C≡C—Ar—, —CH$_2$—Ar—CH$_2$—, —CH$_2$Ar—(CH$_2$)$_2$—, —CH$_2$Ar—CH═CH—, —CH$_2$Ar—C≡C—, —(CH$_2$)$_2$—Ar—(CH$_2$)$_2$—, and the like;

in another embodiment A comprises:
1) a) O; and 0, 1, 2, or 3 —CH$_2$-moieties; or
   b) O; and 0 or 1 —CH$_2$— moieties and —CH═CH— or —C≡C—; and
2) Ar;
e.g., —O—Ar—, —Ar—CH$_2$—O—, —O—Ar—(CH$_2$)$_2$—, —OAr—CH═CH—, —O—Ar—C≡C—, —O—CH$_2$—Ar—, —O—CH$_2$—Ar—(CH$_2$)$_2$, —O—CH$_2$Ar—CH═CH—, —O—CH$_2$Ar—C≡C—, and the like; or in another embodiment A comprises:
1) a) S; and 0, 1, 2, or 3 —CH$_2$— moieties; or
   b) S; and 0 or 1 —CH$_2$— moieties and —CH═CH— or —C≡C—; and
2) Ar;
e.g., —S—Ar—, —Ar—CH$_2$—S—, —S—Ar—(CH$_2$)$_2$—, —SAr—CH═CH—, —S—Ar—C≡C—, —S—CH$_2$—Ar—, —S—CH$_2$-Ar—(CH$_2$)$_2$, —S—CH$_2$Ar—CH═CH—, —S—CH$_2$Ar—C≡C—, and the like.

In another embodiment, the sum of m and o is 2, 3, or 4 wherein one CH$_2$ may be replaced with S or O and 1 —CH$_2$—CH$_2$— may be replaced by —CH═CH— or —C≡C—.

In another embodiment, the sum of m and o is 3 wherein one CH$_2$ may be replaced with S or O and 1 —CH$_2$—CH$_2$— may be replaced by —CH═CH— or —C≡C—.

In another embodiment, the sum of m and o is 2 wherein one CH$_2$ may be replaced with S or O or 1 —CH$_2$—CH$_2$— may be replaced by —CH═CH— or —C≡C—.

In another embodiment, the sum of m and o is 4 wherein one CH$_2$ may be replaced with S or O and 1 —CH$_2$—CH$_2$— may be replaced by —CH═CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. Substitutents of Ar each have from 0 to 4 carbon atoms, from 0 to 3 oxygen atoms, from 0 to 2 sulfur atoms, from 0 to 2 nitrogen atoms, from 0 to 3 fluorine atoms, from 0 to 1 chlorine atoms, from 0 to 1 bromine atoms, from 0 to 1 iodine atoms, and from 0 to 10 hydrogen atoms.

In another embodiment A is —CH$_2$—Ar—OCH$_2$—. In another embodiment A is —CH$_2$-Ph-CH$_2$—. In another embodiment, Ph is attached at the 1 and 3 positions, otherwise known as m-interphenylene, such as when A has the structure shown below.

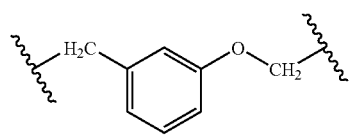

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one —CH$_2$— may be replaced with S or O.

In another embodiment A is —(CH$_2$)$_6$—, C is —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In one embodiment, Ar is thienyl.

In other embodiments, A has one of the following structures.

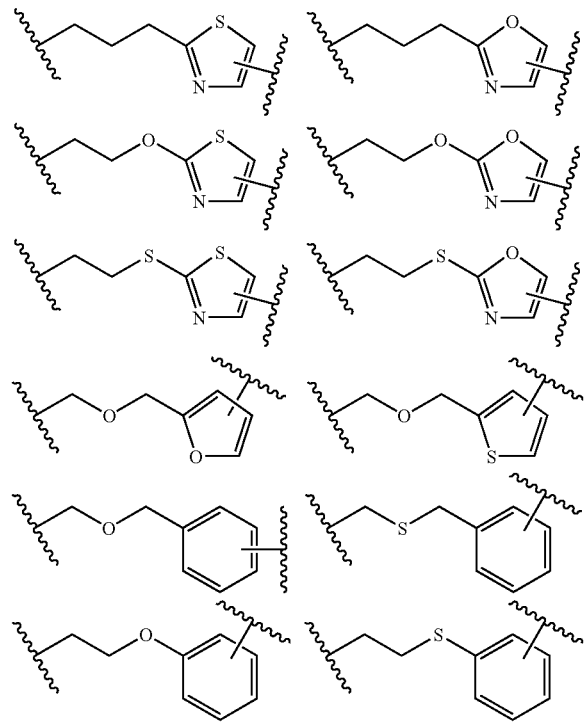

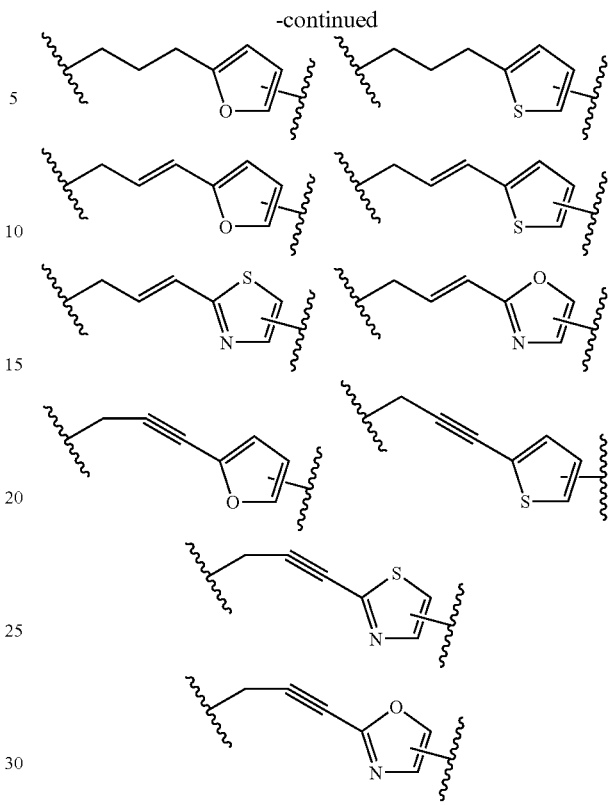

In another embodiment A is —CH$_2$OCH$_2$Ar—.
In another embodiment A is —CH$_2$SCH$_2$Ar—.
In another embodiment A is —(CH$_2$)$_3$Ar—.
In another embodiment A is —CH$_2$—O—(CH$_2$)$_4$—.
In another embodiment A is —CH$_2$S(CH$_2$)$_4$—.
In another embodiment A is —(CH$_2$)$_6$—.
In another embodiment A is cis —CH$_2$CH═CH—(CH$_2$)$_3$—.
In another embodiment A is —CH$_2$C—C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH═CH—CH$_2$OCH$_2$—.
In another embodiment A is —CH$_2$C≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.

In another embodiment A is 4-methoxybutyl.

In another embodiment A is 5-(methoxymethyl)furan-2-yl.

In another embodiment A is 5-(methoxymethyl)thiophen-2-yl.

In another embodiment A is 5-(3-propyl)furan-2-yl.

In another embodiment A is 5-(3-propyl)thiophen-2-yl.

In another embodiment A is 6-hexyl.

In another embodiment A is (Z)-6-hex-4-enyl.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2$$^-$K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;

hydrocarbyloxy up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

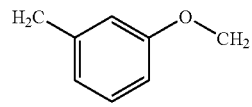

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

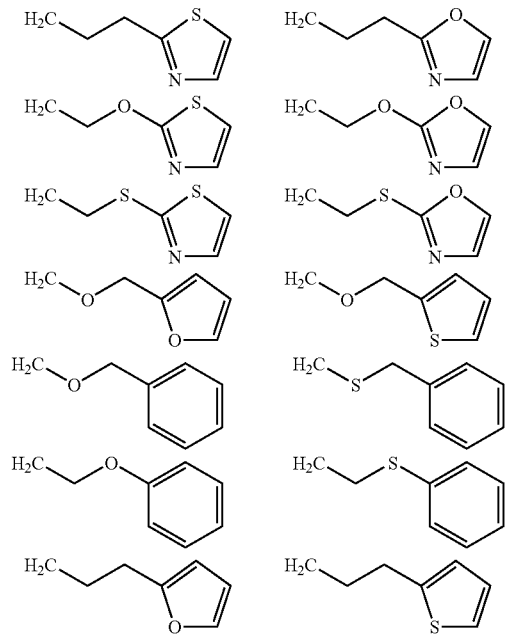

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$—O—(CH$_2$)$_4$.
In another embodiment A is —CH$_2$S(CH$_2$)$_4$.
In another embodiment A is —(CH$_2$)$_6$—.
In another embodiment A is cis —CH$_2$CH═CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH═CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.

In another embodiment A is —CH$_2$—O—(CH$_2$)$_4$—.

In another embodiment A is —CH$_2$—O—CH$_2$—Ar—, wherein Ar is 2,5-interthienylene.

In another embodiment A is —CH$_2$—O—CH$_2$—Ar—, wherein Ar is 2,5-interfurylene.

In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-methoxymethyl)phenyl.
In another embodiment A is 3-(3-propylphenyl.
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.

Compounds according to the each of the structures depicted below, and pharmaceutically acceptable salts thereof, and prodrugs thereof, are contemplated as individual embodiments. In other words, each structure represents a different embodiment.

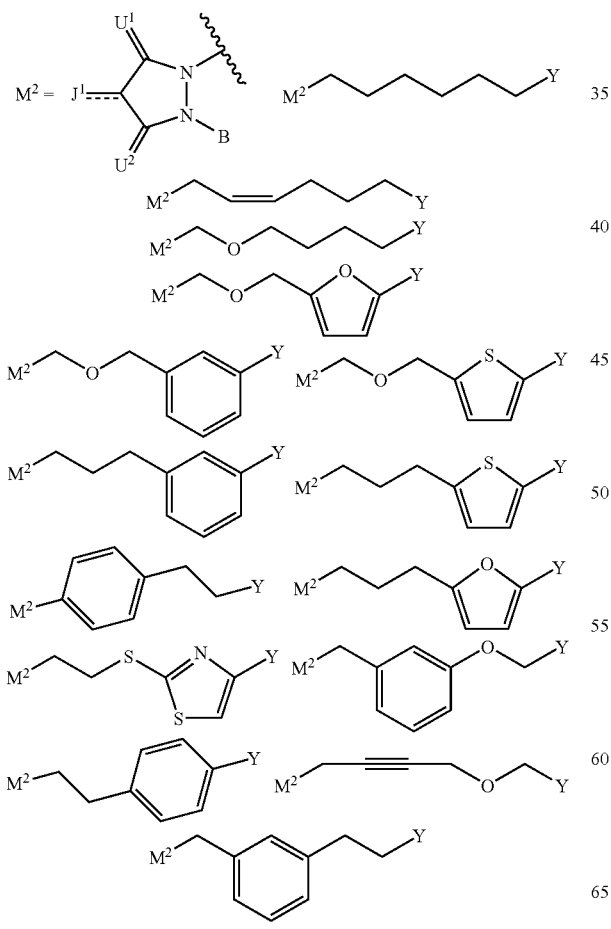

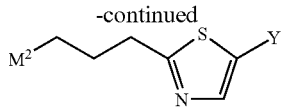

J1 is H; O; OH; O-alkyl having 1, 2, 3, 4, 5 or 6 carbon atoms; alkyl having 1, 2, 3, 4, 5, or 6 carbon atoms; F; Cl; Br; I; CN; or CF3. Thus, each structure depicted below represents a compound embodiment which is individually contemplated. Pharmaceutically acceptable salts and prodrugs of compounds according to the structures below are also contemplated.

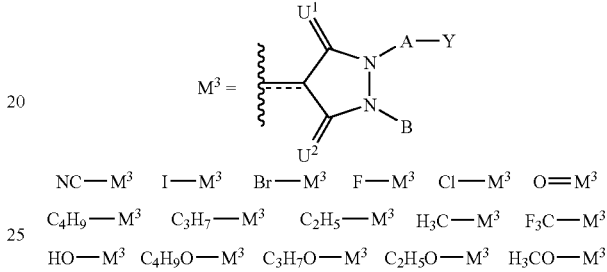

U1 and U2 are independently hydrogen, O, or S. Thus, each structure depicted below represents a compound embodiment which is individually contemplated. Pharmaceutically acceptable salts and prodrugs of compounds according to the structures below are also contemplated.

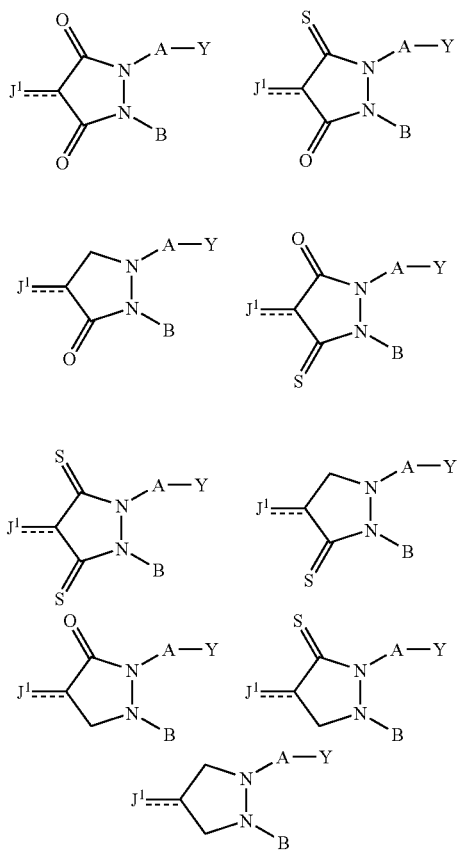

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound to be useful as described herein. In addition to the atoms listed above, a substituent may also have a metal cation or other stable cation having an atom not listed above if the substituent is acidic and the salt form is stable. For example, —OH may form an —O⁻Na⁺ salt or $CO_2H$ may form a $CO_2^-K^+$ salt. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as $OCH_3$, $OCH_2CH_3$, O-cyclohexyl, etc, up to 19 carbon atoms;

other ether substituents such as $CH_2OCH_3$, $(CH_2)_2OCH(CH_3)_2$, and the like;

thioether substituents including S-hydrocarbyl and other thioether substituents;

hydroxyhydrocarbyl, meaning hydrocarbyl-OH such as $CH_2OH$, $C(CH_3)_2OH$, etc, up to 19 carbon atoms;

nitrogen substituents such as $NO_2$, CN, and the like, including amino, such as $NH_2$, $NH(CH_2CH_3OH)$, $NHCH_3$, and the like;

carbonyl substituents, such as $CO_2H$, ester, amide, and the like;

halogen, such as chloro, fluoro, bromo, and the like fluorocarbyl, such as $CF_3$, $CF_2CF_3$, etc.;

phosphorous substituents, such as $PO_3^{2-}$, and the like;

sulfur substituents, including S-hydrocarbyl, SH, $SO_3H$, $SO_2$-hydrocarbyl, $SO_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, $NO_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl. For this type of polycyclic ring system, an aromatic or heteroaromatic ring, not a non-aromatic ring, must be attached to the remainder of the molecule, i.e. the part of the molecule that is not B. In other words, in any structure depicting —B herein, where—is a bond, the bond is a direct bond to an aromatic ring.

In one embodiment, B is substituted aryl or heteroaryl.

In another embodiment B is substituted phenyl.

In another embodiment B has no halogen atoms.

In another embodiment B is 4-(1-hydroxy-2,2-dimethylpropyl)phenyl.

In another embodiment B is 4-(1-hydroxy-2-methylpropan-2-yl)phenyl.

In another embodiment B is 4-(1-hydroxy-2-methylpropyl)phenyl.

In another embodiment B is 4-(1-hydroxybutyl)phenyl.

In another embodiment B is 4-(1-hydroxyheptyl)phenyl.

In another embodiment B is 4-(1-hydroxyhexyl)phenyl.

In another embodiment B is 4-(1-hydroxypentyl)phenyl.

In another embodiment B is 4-(1-hydroxypropyl)phenyl.

In another embodiment B is 4-(3-hydroxy-2-methylheptan-2-yl)phenyl.

In another embodiment B is 4-(3-hydroxy-2-methyloctan-2-yl)phenyl.

In another embodiment B is 1-hydroxy-2,3-dihydro-1H-inden-5-yl.

In another embodiment B is 2,3-dihydro-1H-inden-5-yl.

In another embodiment B is 3-(hydroxy(1-propylcyclobutyl)methyl)phenyl.

In another embodiment B is 4-(1-hydroxy-5,5-dimethylhexyl)phenyl.

In another embodiment B is 4-(hydroxy(1-propylcyclobutyl)methyl)phenyl.

In another embodiment B is 4-tert-butylphenyl.

In another embodiment B is 4-hexylphenyl.

In another embodiment B is 4-(1-hydroxy-2-phenylethyl)phenyl.

In another embodiment B is 4-(1-hydroxy-3-phenylpropyl)phenyl.

In another embodiment B is 4-(1-hydroxycyclobutyl)phenyl.

In another embodiment B is 4-(2-cyclohexyl-1-hydroxyethyl)phenyl.

In another embodiment B is 4-(3-cyclohexyl-1-hydroxypropyl)phenyl.

In another embodiment B is 4-(cyclohexyl(hydroxy)methyl)phenyl.

In another embodiment B is 4-(cyclohexylmethyl)phenyl.

In another embodiment B is 4-(hydroxy(phenyl)methyl)phenyl.

Another embodiment is a compound according to the structure

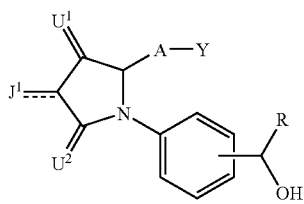

or a pharmaceutical salt thereof, or a prodrug thereof, wherein R is hydrogen or $C_{1-10}$ hydrocarbyl.

Another embodiment is a compound according to the structure

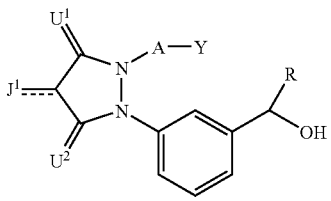

or a pharmaceutical salt thereof, or a prodrug thereof, wherein R is hydrogen or $C_{1-10}$ hydrocarbyl.

Another embodiment is a compound according to the structure

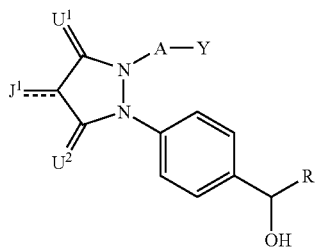

or a pharmaceutical salt thereof, or a prodrug thereof, wherein R is hydrogen or $C_{1-10}$ hydrocarbyl.

Another embodiment is a compound according to the structure

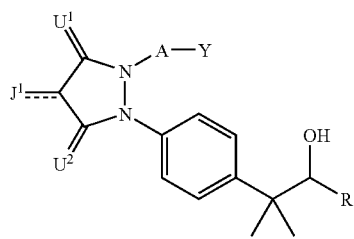

"C1-C10" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylyalkyl is alkyl which is substituted with aryl. In other words alkyl connects aryl to the remaining part of the molecule. Examples are —$CH_2$-Phenyl, —$CH_2$—$CH_2$-Phenyl, and the like. Arylalkyl may or may not be hydrocarbyl, depending upon whether the aryl portion has substituents with heteroatoms.

Unconjugated dienes or polyenes have one or more double bonds which are not conjugated. They may be linear, branched, or cyclic, or a combination thereof.

Combinations of the above are also possible.

Thus, each of the structures below is contemplated. These structures, or pharmaceutically acceptable salts thereof, or prodrugs thereof, individually represent a compound which is an embodiment contemplated herein. In other words, each structure represents a different embodiment.

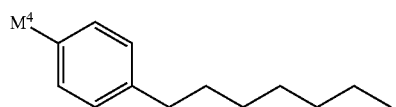

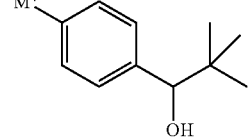

-continued
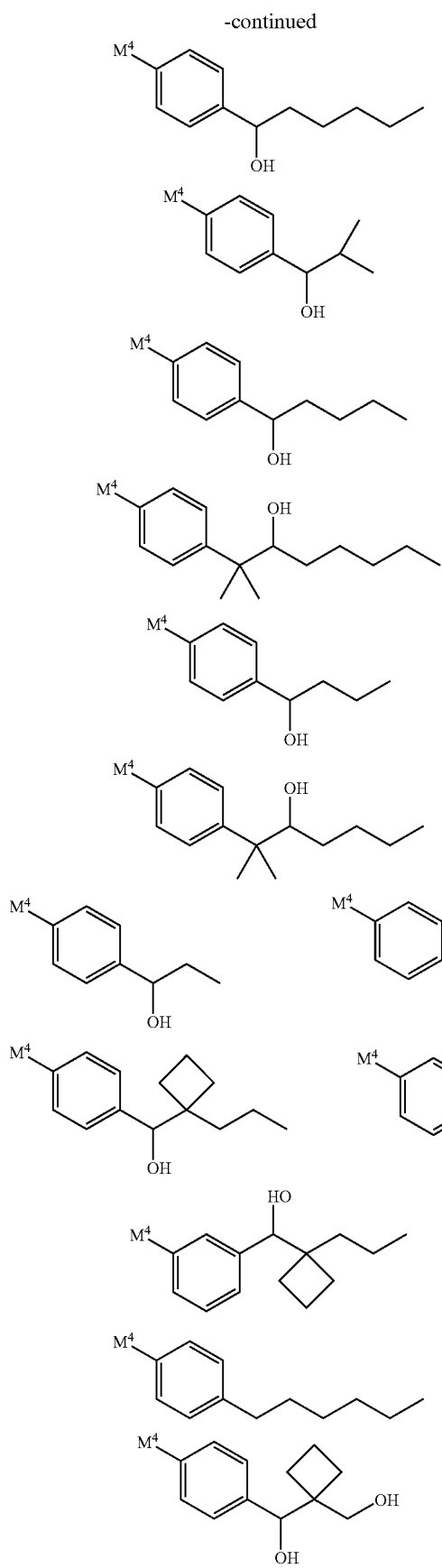
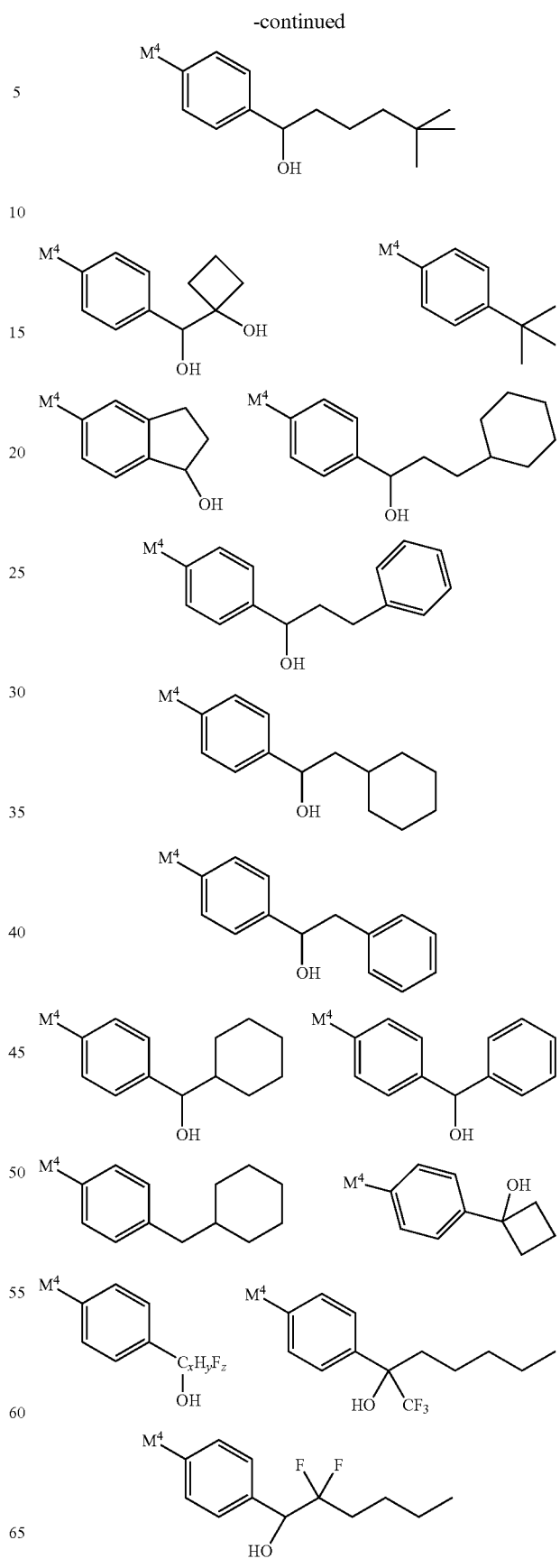

-continued
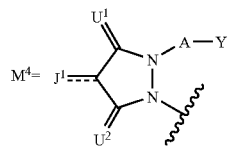
In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.
Hypothetical examples of useful compounds are shown below.
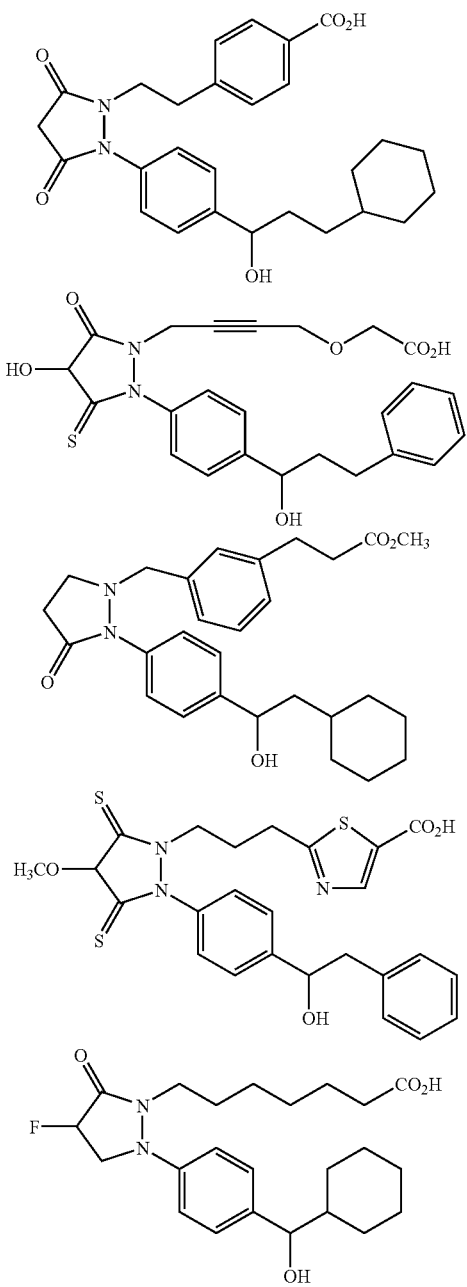
-continued
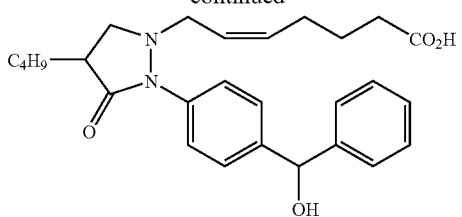
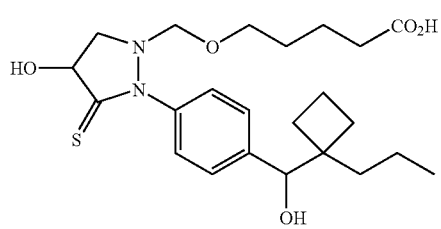
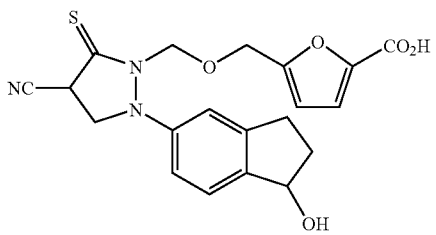
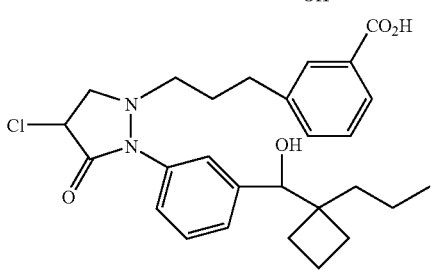
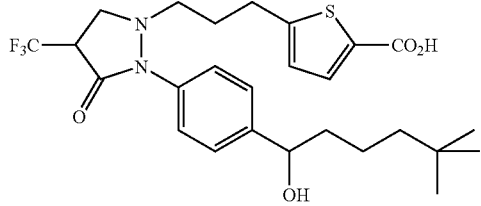
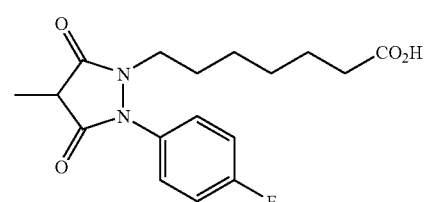
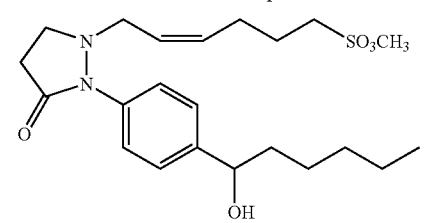

25
-continued
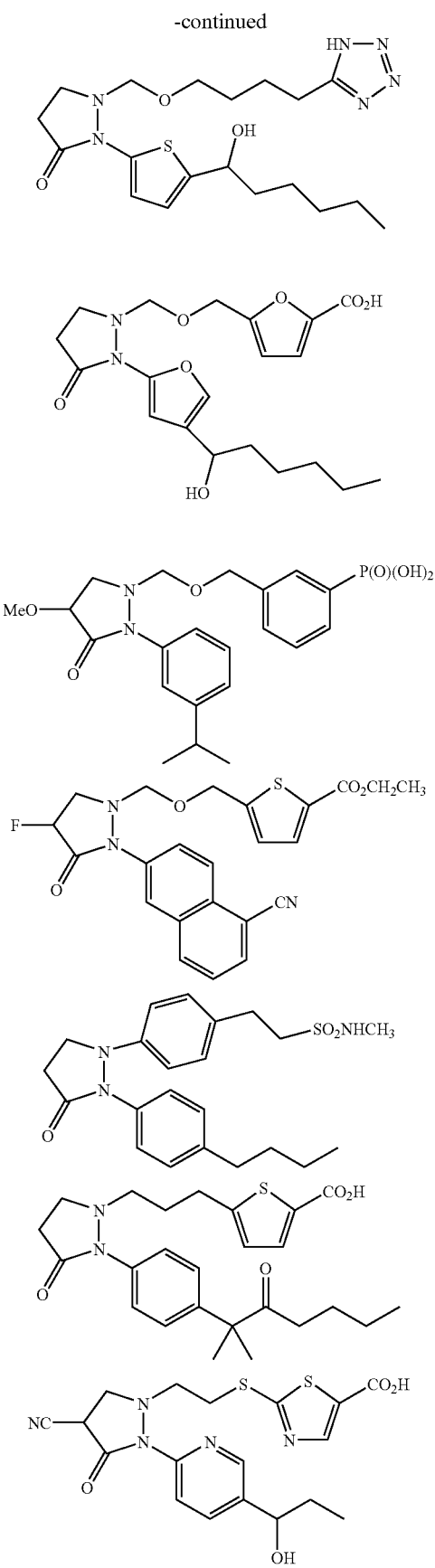
26
-continued
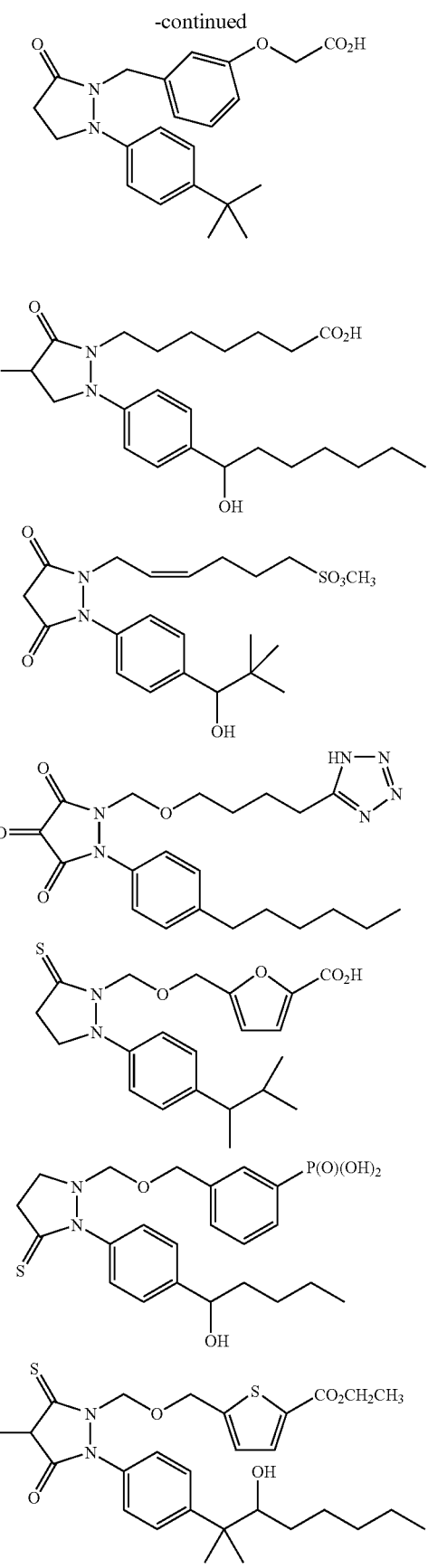

-continued

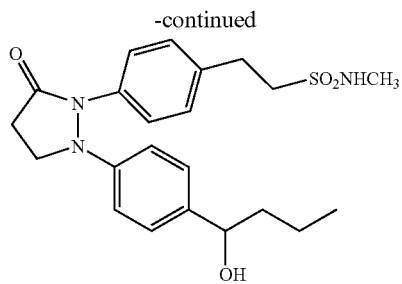

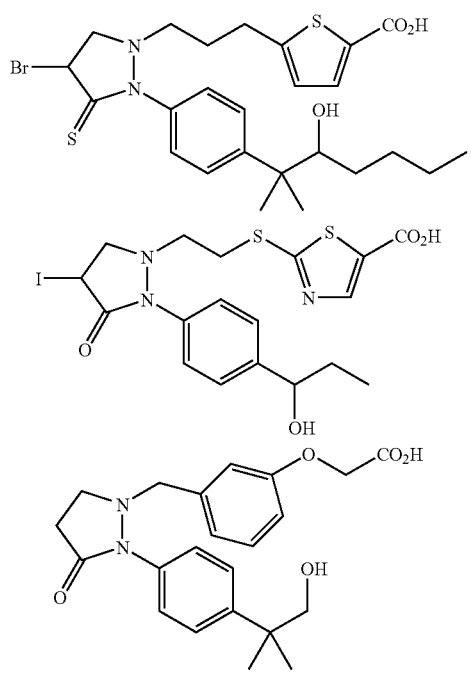

COMPOUND EXAMPLES

The following are hypothetical examples of useful compounds:

Compound Example 1

A compound having a structure

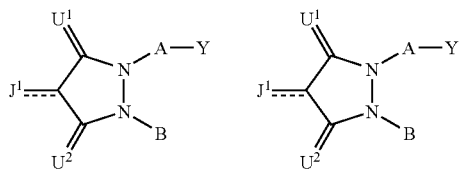

or a pharmaceutically acceptable salt thereof, or a prodrug thereof;

wherein a dashed line represents the presence or absence of a bond;

Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is $-(CH_2)_6-$, cis $-CH_2CH=CH-(CH_2)_3-$, or $-CH_2C\equiv C-(CH_2)_3-$, wherein 1 or 2 carbon atoms may be replaced by S or O; or A is $-(CH_2)_m-Ar-(CH_2)_o-$ wherein Ar is interarylene or heterointerarylene, the sum of m and o is 1, 2, 3, or 4, and wherein 1 $-CH_2-$ may be replaced by S or O, and 1 $-CH_2-CH_2-$ may be replaced by $-CH=CH-$ or $-C\equiv C-$;

$U^1$ and $U^2$ are independently hydrogen, O, or S;

$J^1$ is H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$; and B is substituted aryl or substituted heteroaryl.

Compound Example 2

The compound according to compound example 1 wherein Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

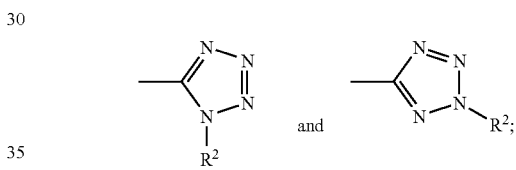

wherein $R^2$ is independently H, $C_1$-$C_6$ alkyl, unsubstituted phenyl, or unsubstituted biphenyl.

Compound Example 3

The compound according to compound example 1 or 2 wherein B is substituted phenyl.

Compound Example 4

The compound according to compound example 1 or 2 having a structure

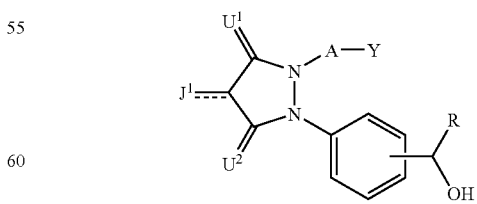

or a pharmaceutically acceptable salt thereof, or a prodrug thereof, wherein R is hydrogen or $C_{10}$ hydrocarbyl.

Compound Example 5

The compound according to compound example 4 wherein R is alkyl.

Compound Example 6

The compound according to compound example 4 wherein R is arylalkyl.

Compound Example 7

The compound according to compound example any one of compound examples 1 to 6 having a structure

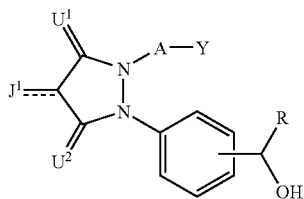

or a pharmaceutically acceptable salt thereof, or a prodrug thereof;
wherein R is hydrogen or $C_{1-10}$ hydrocarbyl.

Compound Example 8

The compound according to compound example 1 or 2 wherein A is (3-methylphenoxy)methyl.

Compound Example 9

The compound according to compound example 1 or 2 wherein A is (4-but-2-ynyloxy)methyl.

Compound Example 10

The compound according to compound example 1 or 2 wherein A is 2-(2-ethylthio)thiazol-4-yl.

Compound Example 11

The compound according to compound example 1 or 2 wherein A is 2-(3-propyl)thiazol-5-yl.

Compound Example 12

The compound according to compound example 1 or 2 wherein A is 3-methoxymethyl)phenyl.

Compound Example 13

The compound according to compound example 1 or 2 wherein A is 3-(3-propylphenyl.

Compound Example 14

The compound according to compound example 1 or 2 wherein A is 3-methylphenethyl.

Compound Example 15

The compound according to compound example 1 or 2 wherein A is 4-(2-ethyl)phenyl.

Compound Example 16

The compound according to compound example 1 or 2 wherein A is 4-phenethyl.

Compound Example 17

The compound according to compound example 1 or 2 wherein A is 4-methoxybutyl.

Compound Example 18

The compound according to compound example 1 or 2 wherein A is 5-(methoxymethyl)furan-2-yl.

Compound Example 19

The compound according to compound example 1 or 2 wherein A is 5-(methoxymethyl)thiophen-2-yl.

Compound Example 20

The compound according to compound example 1 or 2 wherein A is 5-(3-propyl)furan-2-yl.

Compound Example 21

The compound according to compound example 1 or 2 wherein A is 5-(3-propyl)thiophen-2-yl.

Compound Example 22

The compound according to compound example 1 or 2 wherein A is 6-hexyl.

Compound Example 23

The compound according to compound example 1 or 2 wherein A is (Z)-6-hex-4-enyl.

Compound Example 24

The compound according to any one of compound examples 1, 2, and 8-23 wherein B is 4-(1-hydroxy-2,2-dimethylpropyl)phenyl.

Compound Example 25

The compound according to any one of compound examples 1, 2, and 8-23 wherein B is 4-(1-hydroxy-2-methylpropan-2-yl)phenyl.

Compound Example 26

The compound according to any one of compound examples 1, 2, and 8-23 wherein B is 4-(1-hydroxy-2-methylpropyl)phenyl.

Compound Example 27

The compound according to any one of compound examples 1, 2, and 8-23 wherein B is 4-(1-hydroxybutyl)phenyl.

Compound Example 28

The compound according to any one of compound examples 1, 2, and 8-23 wherein B is 4-(1-hydroxyheptyl)phenyl.

Compound Example 29

The compound according to any one of compound examples 1, 2, and 8-23 wherein B is 4-(1-hydroxyhexyl)phenyl.

Compound Example 30

The compound according to any one of compound examples 1, 2, and 8-23 wherein B is 4-(1-hydroxypentyl)phenyl.

Compound Example 31

The compound according to any one of compound examples 1, 2, and 8-23 wherein B is 4-(1-hydroxypropyl)phenyl.

Compound Example 32

The compound according to any one of compound examples 1, 2, and 8-23 wherein B is 4-(3-hydroxy-2-methylheptan-2-yl)phenyl.

Compound Example 33

The compound according to any one of compound examples 1, 2, and 8-23 wherein B is 4-(3-hydroxy-2-methyloctan-2-yl)phenyl.

Compound Example 34

The compound according to any one of compound examples 1, 2, and 8-23 wherein B is 1-hydroxy-2,3-dihydro-1H-inden-5-yl.

Compound Example 35

The compound according to any one of compound examples 1, 2, and 8-23 wherein B is 2,3-dihydro-1H-inden-5-yl.

Compound Example 36

The compound according to any one of compound examples 1, 2, and 8-23 wherein B is 3-(hydroxy(1-propylcyclobutyl)methyl)phenyl.

Compound Example 37

The compound according to any one of compound examples 1, 2, and 8-23 wherein B is 4-(1-hydroxy-5,5-dimethylhexyl)phenyl.

Compound Example 38

The compound according to any one of compound examples 1, 2, and 8-23 wherein B is 4-(hydroxy(1-propylcyclobutyl)methyl)phenyl.

Compound Example 39

The compound according to any one of compound examples 1, 2, and 8-23 wherein B is 4-tert-butylphenyl.

Compound Example 40

The compound according to any one of compound examples 1, 2, and 8-23 wherein B is 4-hexylphenyl.

Compound Example 41

The compound according to any one of compound examples 1, 2, and 8-23 wherein B is 4-(1-hydroxy-2-phenylethyl)phenyl.

Compound Example 42

The compound according to any one of compound examples 1, 2, and 8-23 wherein B is 4-(1-hydroxy-3-phenylpropyl)phenyl.

Compound Example 43

The compound according to any one of compound examples 1, 2, and 8-23 wherein B is 4-(1-hydroxycyclobutyl)phenyl.

Compound Example 44

The compound according to any one of compound examples 1, 2, and 8-23 wherein B is 4-(2-cyclohexyl-1-hydroxyethyl)phenyl.

Compound Example 45

The compound according to any one of compound examples 1, 2, and 8-23 wherein B is 4-(3-cyclohexyl-1-hydroxypropyl)phenyl.

Compound Example 46

The compound according to any one of compound examples 1, 2, and 8-23 wherein B is 4-(cyclohexyl(hydroxy)methyl)phenyl.

Compound Example 47

The compound according to any one of compound examples 1, 2, and 8-23 wherein B is 4-(cyclohexylmethyl)phenyl.

Compound Example 48

The compound according to any one of compound examples 1, 2, and 8-23 wherein B is 4-(hydroxy(phenyl)methyl)phenyl.

Compound Example 49

The compound according to any one of compound examples 1 to 48 wherein $J^1$ is H.

Compound Example 50

The compound according to any one of compound examples 1 to 48 wherein $J^1$ is O.

Compound Example 51

The compound according to any one of compound examples 1 to 48 wherein $J^1$ is OH.

Compound Example 52

The compound according to any one of compound examples 1 to 48 wherein $J^1$ is O-alkyl having 1, 2, 3, 4, 5 or 6 carbon atoms.

Compound Example 53

The compound according to any one of compound examples 1 to 48 wherein $J^1$ is alkyl having 1, 2, 3, 4, 5, or 6 carbon atoms.

Compound Example 54

The compound according to any one of compound examples 1 to 48 wherein $J^1$ is F.

Compound Example 55

The compound according to any one of compound examples 1 to 48 wherein $J^1$ is Cl.

Compound Example 56

The compound according to any one of compound examples 1 to 48 wherein $J^1$ is Br.

Compound Example 57

The compound according to any one of compound examples 1 to 48 wherein $J^1$ is I.

Compound Example 58

The compound according to any one of compound examples 1 to 48 wherein $J^1$ is CN.

Compound Example 59

The compound according to any one of compound examples 1 to 48 wherein $J^1$ is $CF_3$,

Compound Example 60

The compound according to any one of compound embodiments 1 to 59 wherein $U^1$ is H.

Compound Example 61

The compound according to any one of compound embodiments 1 to 59 wherein $U^1$ is O.

Compound Example 62

The compound according to any one of compound embodiments 1 to 59 wherein $U^1$ is S.

Compound Example 63

The compound according to any one of compound embodiments 1 to 62 wherein $U^2$ is H.

Compound Example 64

The compound according to any one of compound embodiments 1 to 62 wherein $U^2$ is O.

Compound Example 65

The compound according to any one of compound embodiments 1 to 62 wherein $U^2$ is S.

The following are hypothetical examples of compositions, kits, methods, uses, and medicaments employing the hypothetical compound examples.

Composition Example

A composition comprising a compound according to any one of compound examples 1 to 65, wherein said composition is a liquid which is ophthalmically acceptable.

Medicament Examples

Use of a compound according to any one of compound examples 1 to 65 in the manufacture of a medicament for the treatment of glaucoma or ocular hypertension in a mammal.

Use of a compound according to any one of compound examples 1 to 65 in the manufacture of a medicament for the treatment of baldness in a person.

A medicament comprising a compound according to any one of compound examples 1 to 65, wherein said composition is a liquid which is ophthalmically acceptable.

Method Example

A method comprising administering a compound according to any one of compound examples 1 to 65 to a mammal for the treatment of glaucoma or ocular hypertension.

Kit Example

A kit comprising a composition comprising compound according to any one of compound examples 1 to 65, a container, and instructions for administration of said composition to a mammal for the treatment of glaucoma or ocular hypertension.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

Synthetic Methods

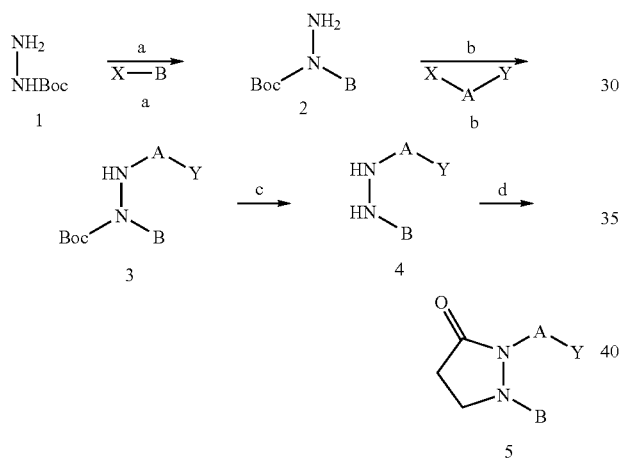

(a) a, CuI, MeN(H)CH$_2$CH$_2$N(H)Me, K$_2$CO$_3$, MeCN; (b) NaH, b, DMF; (c) TFA, CH$_2$Cl$_2$; (d) 3-chloropropionyl chloride, K$_2$CO$_3$, DMF.

While there are many ways the compounds disclosed herein, one exemplary synthesis may begin with commercially available N-Boc hydrazine (1, also known as t-butyl carbazate, Aldrich Chemical Company, see Scheme 1). N-arylation occurs to give 2 according to Buchwald's copper-catalyzed procedure (Org. Lett. 2001, 3, 3803-3805) using a wide variety of substituted bromophenyl and other bromoaryl compounds a. The haloarenes a are either available commercially or may be made according to published literature procedures. For example, U.S. patent application Ser. No. 11/009,298, filed on Dec. 10, 2004 and U.S. Provisional Patent Application 60/742,779 filed on Dec. 6, 2005, both of which are expressly incorporated by reference herein, disclose methods of making a number of useful substituted bromophenyl compounds. These procedures may also be readily adapted to other bromoaryl compounds such as substituted bromothienyl, substituted bromofuryl, substituted bromopyridinyl, substituted bromonaphthyl, substituted bromobenzothienyl, and the like. Intermediate 2 is then alkylated on N' using electrophiles b to provide intermediate 3.

Examples of b include ethyl 7-bromoheptanoate (commercially available from Aldrich Chemical Company) and methyl 7-bromohept-5-ynoate (Org. Synth. 1993, Collect. Vol. VIII, 415-420). Examples of b also include electrophiles bearing aryl and heteroaryl groups (e.g. methyl 4-(2-bromoethyl)benzoate [available in one step from commercially available 4-(2-bromoethyl)benzoic acid] and methyl 5-(3-bromopropyl)-thiophene-2-carboxylate [see WO 2004/037786, incorporated by reference herein]). Other methods of preparing b are readily ascertained by those of ordinary skill in the art based upon this disclosure.

Intermediate 3 is then deprotected to give intermediate 4 which is treated with 3-chloropropionyl chloride (using the method of Araldi, et al., US 2004/0254233) to give product 5. Compound 5 may be the target compound, or may require deprotection(s) and/or functionalization (depending on the nature of B and Y) to arrive at the target compound.

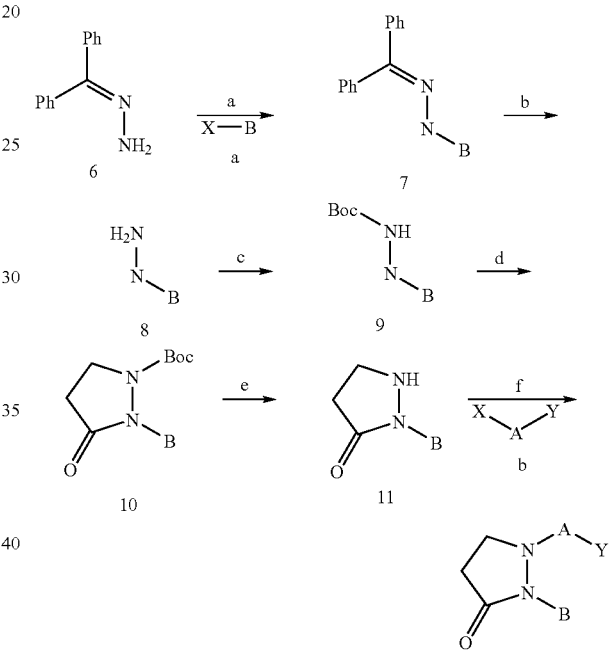

(a) a, Pd(OAc)$_2$, BINAP, NaOt-Bu, toluene; (b) TsOH, H$_2$O, EtOH; (c) BOC$_2$O, CH$_2$Cl$_2$; (d) chloropropionyl chloride, K$_2$CO$_3$, DMF; (e) TFA, CH$_2$Cl$_2$; (f) NaH, b, DMF.

In another hypothetical example, benzophenone hydrazone (6, Aldrich chemical company) serves as the stating material (see Scheme 2). In this case, N'-arylation occurs to give 7 according to Buchwald's palladium-catalyzed procedure (J. Am. Chem. Soc. 1998, 120, 6621-6622) using a wide variety of substituted bromophenyl and other bromoaryl compounds a. Deprotection reveals the aryl hydrazine 8 which is protected to give N-Boc-N'-aryl hydrazine 9. A large variety of substituted aryl hydrazines such as 8 are commercially available. Treatment of 9 with 3-chloropropionyl chloride (using the method of Araldi, et al., US 2004/0254233) gives intermediate 10 which is then deprotected and alkylated on nitrogen to afford product 12. Compound 12 may be the target compound, or may require deprotection(s) and/or functionalization (depending on the nature of B and Y) to arrive at the target compound.

Intermediates 2 and 9 are regioisomers. In certain cases, the copper chemistry used to arrive at 2 will also afford compound 9 (see Buchwald, above, and Buchwald, *J. Am. Chem. Soc.* 2001, 123, 7727-7729). Palladium-catalyzed arylation may also afford mixtures of regioisomers (Wang, et al., *Tetrahedron Lett.* 1999, 40, 3543-3546), mainly favoring isomer 2. This represents an alternative approach to compound 9.

In another hypothetical example (scheme 3), intermediate 3 may be cyclized using malonyl chloride (or other activated source of malonate) to afford the pyrazolidine dione 13. This may be the target compound, or may serve as an intermediate to compounds substituted at the carbon adjacent to both ketones such as 14. The ring methylene of dione 13 is alkylated using alkyl electrophiles J by employing a mild base such as potassium carbonate using the method of Vennerstrom and Holmes, *J. Med. Chem.* 1987, 30, 563-567. Chlorination (J=Cl) may be accomplished using the method of Pesin et al. *Z. Obshch. Khim.* 1958, 20, 2816-2820. Other electrophiles known in the art can be envisioned to introduce other J groups (e.g. the Davis oxaziridine reagent or other suitable reagent for J=OH and $Br_2$ or NBS for J=Br). As an alternative, J may be introduced into the malonate derivative prior to reaction with compound 4. As halogens such as Cl and Br are useful as nucleophilic substitution leaving groups, they provide a means for reaching other J groups using the nucleophile J⁻ or a synthetic equivalent thereof. Compounds wherein J is OH may also be derivatized with triflate, tosylate, or the like to provide good leaving groups for nucleophilic substitution. For example, J=CN may be reached in this manner. These procedures are well known in the art.

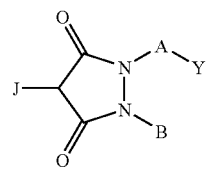

(a) $CH_2(COCl)_2$, $Et_3N$, dioxane; (b) c, $K_2CO_3$, DMF.

The carbon adjacent to the ketone in pyrazolidinones 5 and 12 may be alkylated using alkyl electrophiles J by employing LDA as the base (e.g. Hiasta et al., *J. Med. Chem.* 1991, 34, 1560-1570) (Scheme 4). Other J groups may be introduced using LDA and the electrophiles discussed above for scheme 3. As an alternative, J may be introduced into the chloropropionate derivative prior to reaction with compound 4 or compound 9.

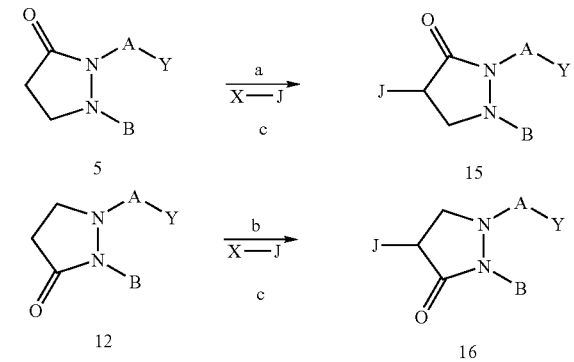

(a) c, LDA, THF.

A carbonyl oxygen may be replaced with sulfur using Lawesson's reagent or other methods. Thus, compounds wherein $J^1$, $U^1$ and/or $U^2$ are S may be prepared.

The steps of these synthetic procedures may also be rearranged. For example in Scheme 1, N'-alkylation may take place prior to amide N-arylation. It is also envisioned that chloro- or iodo-arenes may be employed in place of the bromoarenes described above. The requisite chloro- or iodo-arenes may be prepared by procedures analogous to those used to prepare the bromoarenes. Alternative starting materials to N-Boc hydrazine and benzophenone hydrazone include commercially available 3-pyrazolidinone HCl (see Scheme 5 and example 1) and 3,5-pyrazolidine dione.

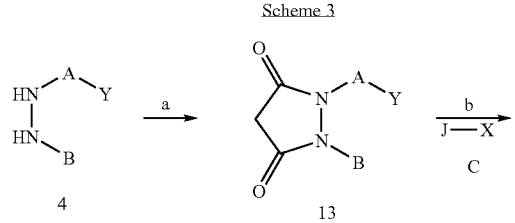

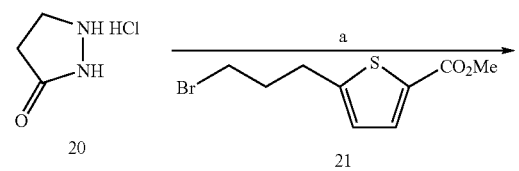

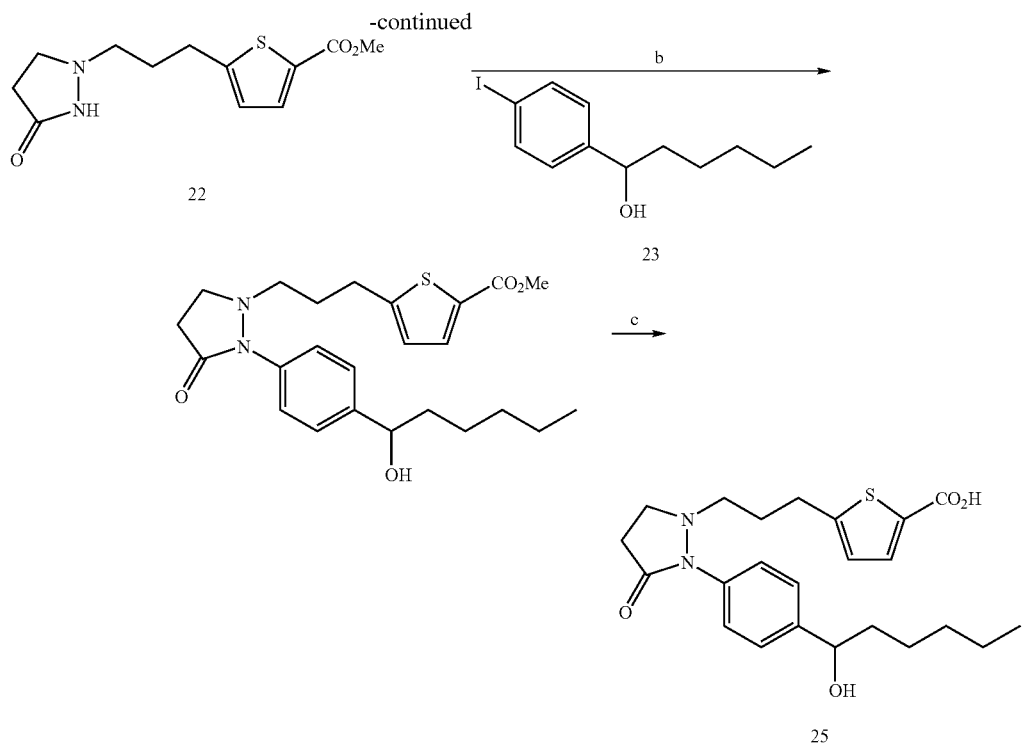

(a) K2CO3, DMF, rt; (b) CuI, 1,10-phenanthroline, Cs2CO3, DMF, 80° C.; (c) LiOH (aq.), THF, 40° C.

Example 1

5-(3-(2-(4-(1-hydroxyhexyl)phenyl)-3-oxopyrazolidin-1-yl) propyl)thiophene-2-carboxylic Acid (25)

Step 1. Alkylation of 20 with 21 to give 22

Potassium carbonate (8.28 g, 60.0 mmol), methyl 5-(3-bromopropyl)-thiophene-2-carboxylate (21, for preparation, see Billot, X. et al WO2004/037786, incorporated by reference herein, 5.66 g, 21.5 mmol), 3-pyrazolidinone HCl (20, 2.57 g, 21.0 mmol) and DMF (25 mL) were combined under argon and stirred at rt. After 3 d at rt, HPLC analysis indicated the reaction to be complete and EtOAc (100 mL) was added. The mixture was washed with water (2×75 mL). The combined aqueous phase was back-extracted with EtOAc (50 mL). The combined organic phase was washed with brine (75 mL), filtered through filter paper and concentrated in vacuo to afford 7.5 g of a crude oil. Purification of the crude product by flash column chromatography on 75 g silica gel (50% $CH_2Cl_2$/hexane→$CH_2Cl_2$→20% EtOAc/$CH_2Cl_2$→100% EtOAc→10% MeOH/EtOAc, gradient) afforded 3.2 g (57%) of 22 which solidified on standing.

Step 2. Arylation of 22 with 23 to give 24

Cesium carbonate (4.89 g, 15.0 mmol), copper (I) iodide (19 mg, 0.10 mmol), 1,10-phenanthroline (180 mg, 1.0 mmol), amide 22 (2.88 g, 10.7 mmol) and 1-(4-iodophenyl)hexan-1-ol (23, prepared from 4-iodobenzaldehyde using the method described for the analogous bromoarene in Old and Dinh, WO2006/098918, 3.34 g 11.0 mmol) and DMF (25 mL) were combined into a sealable tube. Argon was bubbled through the mixture for 15 min, the tube was sealed, and the mixture was heated at 80° C. overnight. Upon cooling, HPLC analysis showed no reaction had taken place. More copper (I) iodide (60 mg, 0.32 mmol) and 1,10-phenanthroline (180 mg, 1.0 mmol) was added and the mixture was heated at 80° C. overnight. Upon cooling, HPLC analysis showed the reaction was nearly complete. EtOAc (100 mL) was added and the mixture was filtered through 25 g silica gel, washing the pad with EtOAc (150 mL). The filtrate was concentrated in vacuo to afford 3.7 g of a crude oil. Purification of the crude product by flash column chromatography on 50 g silica gel (hexane→25% $CH_2Cl_2$/hexane→$CH_2Cl_2$→5% EtOAc/$CH_2Cl_2$→25% EtOAc/$CH_2Cl_2$, gradient) afforded 0.29 g (6%) of 24 as a brown oil.

Step 3. Saponification of 24 to Give 25

Lithium hydroxide (0.22 mL of a 1.0 M aqueous solution, 0.22 mmol) was added to a solution of ester 24 (20 mg, 0.045 mmol) in THF (0.22 mL). The solution was heated at 40° C. for 18 h, then cooled to rt. The mixture was partitioned between 1.0 M HCl (1 mL) and EtOAc (5 mL). The phases were separated and the aqueous phase was extracted with EtOAc (2×5 mL). The combined extracts were washed with brine (5 mL), dried ($Na_2SO_4$), filtered and concentrated in vacuo. Purification of the crude residue by column chromatography on 4 g silica gel ($CH_2Cl_2$→20% MeOH/$CH_2Cl_2$) afforded 11 mg (57%) of the title compound.

Based upon this disclosure, numerous other ways of preparing the compounds disclosed herein will be apparent to a person of ordinary skill in the art.

In Vitro Testing

U.S. patent application Ser. No. 11/553,143, filed on Oct. 26, 2006, incorporated by reference herein, describes the methods used to obtain the in vitro data in the table below.

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | Ki | hFP | hEP1 | hEP3A | hTP | hIP | hDP |
| 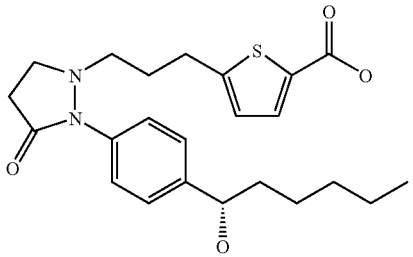 | 79 | 1.8 | 251 | NT | >10000 | NA | NA | 5068 | NA | NA | NA |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound which is a carboxylic acid or a bioisostere thereof, said carboxylic acid having a structure

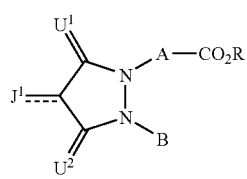

or a pharmaceutically acceptable salt thereof;
wherein a dashed line represents the presence or absence of a bond;
A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—;
$U^1$ and $U^2$ are independently O, or S;
$J^1$ is H; O; OH; O-alkyl having 1, 2, 3, 4, 5 or 6 carbon atoms; alkyl having 1, 2, 3, 4, 5, or 6 carbon atoms; F; Cl; Br; I; CN; or $CF_3$;
B is substituted aryl or substituted heteroaryl; and
R is $C_1$-$C_6$ alkyl or —$CH_2CH_2OH$.

2. The compound of claim 1 wherein Y is selected from $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

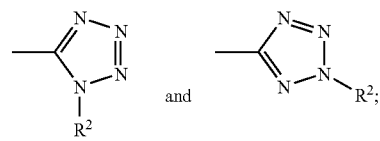

wherein $R^2$ is independently H, $C_1$-$C_6$ alkyl, unsubstituted phenyl, or unsubstituted biphenyl.

3. The compound of claim 1 wherein A has a structure selected from:

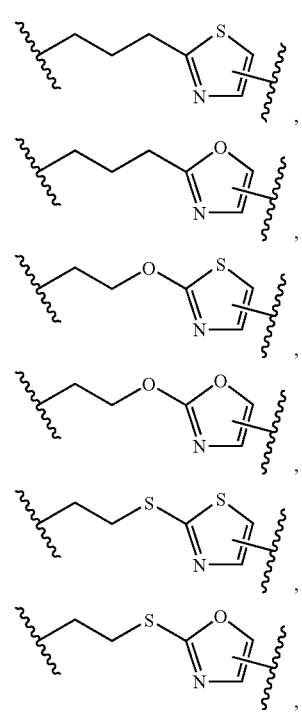

-continued

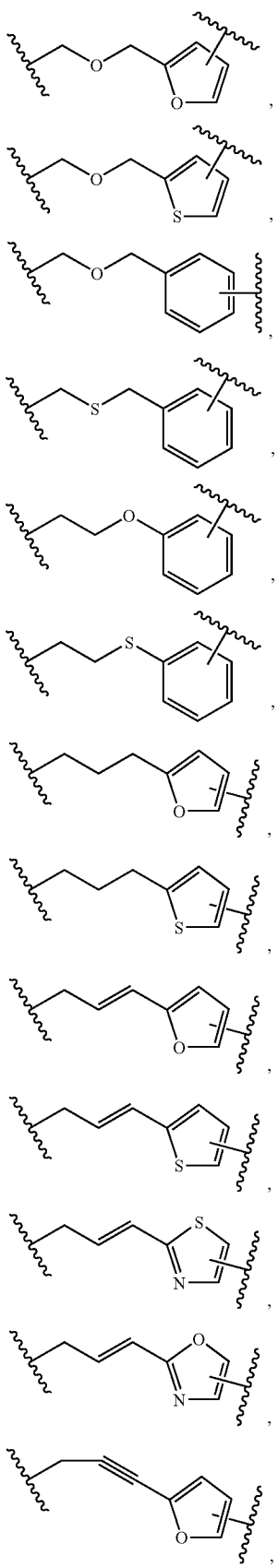

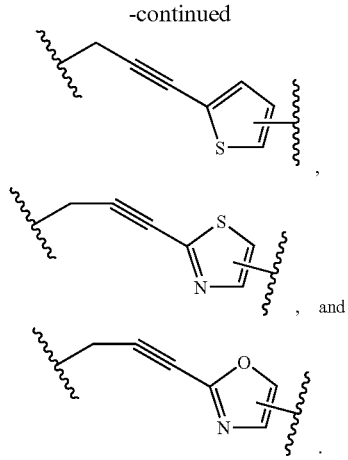

, and

4. The compound of claim 1 wherein A is 5-(3-propyl) thiophen-2-yl, 6-hexyl, or (Z)-6-hex-4-enyl.

5. The compound of claim 1 wherein B is substituted phenyl.

6. The compound of claim 1 wherein R is isopropyl or —CH$_2$CH$_2$OH.

7. The compound of claim 1 having a structure

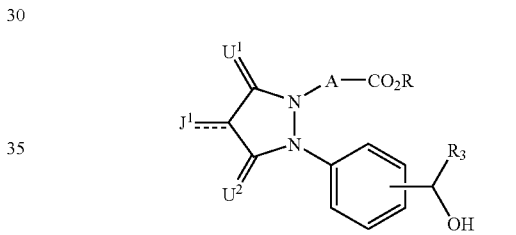

or a pharmaceutically acceptable salt thereof;

wherein R$_3$ is hydrogen or C$_{1-10}$ hydrocarbyl.

8. The compound of claim 7 wherein R is isopropyl or —CH$_2$CH$_2$OH.

9. The compound of claim 1 having a structure

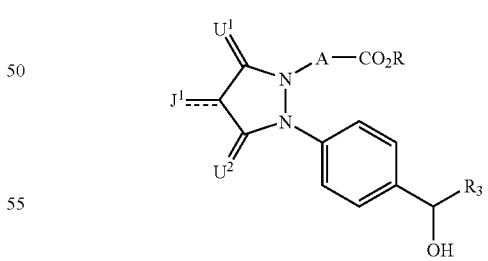

or a pharmaceutically acceptable salt thereof;

wherein R$_3$ is hydrogen or C$_{1-10}$ hydrocarbyl.

10. The compound of claim 1 wherein J is H.

11. The compound of claim 10 wherein U$^1$ is H.

12. The compound of claim 11 wherein U$^2$ is O.

13. The compound of claim 9 wherein R is isopropyl or —CH$_2$CH$_2$OH.

14. A method comprising administering a compound of claim 1 to a mammal for the treatment of glaucoma or ocular hypertension.

15. A kit comprising a composition comprising compound of claim 1, a container, and instructions for administration of said composition to a mammal for the treatment of glaucoma or ocular hypertension.

16. A composition comprising a compound of claim 1, wherein said composition is a liquid which is ophthalmically acceptable.

17. A method comprising administering a compound of claim 1 to a mammal for the treatment of glaucoma or ocular hypertension.

* * * * *